United States Patent [19]
Eriyama et al.

[11] Patent Number: 6,160,067
[45] Date of Patent: Dec. 12, 2000

[54] REACTIVE SILICA PARTICLES, PROCESS FOR MANUFACTURING THE SAME, USE OF THE SAME

[75] Inventors: Yuichi Eriyama, Tsukuba; Atsushi Baba, Tsuchiura; Takashi Ukachi, Ushiku, all of Japan

[73] Assignees: DSM N.V., Heerlen, Netherlands; JSR Corporation; Japan Fine Coatings, both of Tokyo, Japan

[21] Appl. No.: 09/053,625

[22] Filed: Apr. 2, 1998

Related U.S. Application Data

[63] Continuation of application No. PCT/NL96/00381, Oct. 2, 1996.

[30] Foreign Application Priority Data

Oct. 3, 1995 [JP] Japan ..................................... 7-255925

[51] Int. Cl.$^7$ .................................................. C08F 30/08
[52] U.S. Cl. ........................ 526/279; 427/214; 427/220; 427/219
[58] Field of Search .................... 427/220, 214, 427/219; 526/279

[56] References Cited

U.S. PATENT DOCUMENTS 4,151,154  4/1979  Berger .................................. 260/40 R

FOREIGN PATENT DOCUMENTS 0460560  12/1991  European Pat. Off. .
3-014 880  12/1991  Japan .

*Primary Examiner*—David W. Wu
*Assistant Examiner*—Ling-Siu Choi
*Attorney, Agent, or Firm*—Pillsbury Madison & Sutro LLP

[57] ABSTRACT

Reactive silica particles capable of producing coatings exhibiting excellent scratch resistance, weather resistance, adhesiveness, and curability, while satisfying a wide spectrum of performances from transparency to semi-transparency and providing a glossy surface as well as a frosty surface. Reactive silica particles comprises silica particles and an organic compound chemically bonded to the silica particles via a silyloxy group, wherein the organic compound has a polymerizable unsaturated group, a group represented by the following formula (1),

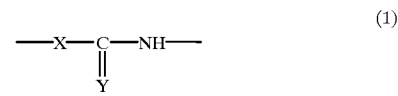

(wherein X is a group selected from —NH—, —O—, and —S— and Y is a group selected from oxygen and sulfur, provided that when X is —O—, Y is a sulfur atom), and a group represented by the following formula (2),

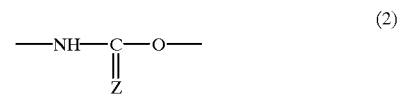

(wherein Z is a group selected from oxygen and sulfur)

12 Claims, No Drawings

REACTIVE SILICA PARTICLES, PROCESS FOR MANUFACTURING THE SAME, USE OF THE SAME

This is a continuation of International Appln. No. PCT/NL96/00381 filed Oct. 2, 1996 which designated the U.S.

DESCRIPTION OF BACKGROUND ART

1. Field of the Invention

The present invention relates to reactive silica, a process for manufacturing the same, and use of the same. More particularly, the present invention relates to reactive silica particles which can provide a curable composition with superior storage stability and capability of producing a coating film on the surfaces of substrates, such as plastics, metals, wood, papers, glasses, slates, or the like. The coating film exhibits excellent characteristics, such as scratch resistance, weather resistance, adhesiveness, and curability. The film can be made to satisfy a wide spectrum of performances from transparent to semi-transparent, and from a glossy surface to a frosty surface. The film can for example be applied to the surface of molded articles made from polymers, such as polycarbonate, polymethacrylate, polyvinyl chloride, polyester or polyolefins, to protect the surface from scratch and contamination. The composition can be used as a material for plastic optical parts and touch panels, film-type liquid crystal elements, hard coatings of plastic molded articles, a photocurable adhesive, a photocurable sealing material, a contamination-proof or scratch-proof coating for building interior materials, a flooring material, a material for walls, or a binder for printing ink.

2. Prior Art

In recent years there is a demand for a material which can be used to make for example coatings that are excellent in characteristics, such as scratch resistance, weather resistance, adhesiveness, and curability, and which can be controlled with respect to the optical characteristics in a wide range from transparent to semi-transparent. Various coating compositions containing colloidal silica have been proposed with an object of improving the scratch resistance of the cured coatings. For example, U.S. Pat Nos. 3,451,838 and 2,404,457 disclose a thermoset coating composition containing an alkoxysilane hydrolyzate and colloidal silica as major components. Japanese Patent Publication (kokoku) No. 21815/1987 discloses a photocurable coating composition containing colloidal silica particles, of which the surface is modified with methacryloxy silane, and acrylate. In these compositions, the surface of silica particles is treated with a specific organic silane compound or under specific conditions to improve their characteristics as a coating material.

These coating materials, however, are not able to meet all the required properties such as constantly producing films which exhibit excellent scratch resistance, weather resistance, adhesiveness, and curability, and furthermore can be formulated to satisfy a wide spectrum of performances from transparency to semi-transparency, and to provide a glossy surface as well as a frosty surface.

In addition, the thermoset coating compositions disclosed, for example, by U.S. Pat. Nos. 3,451,838 and 2,404,357 require a heat treatment at high temperatures for a long time and, therefore, cannot be applied to low heat resistent plastic materials.

SUMMARY OF THE INVENTION

An object of the present invention is to provide reactive silica particles comprising silica particles and an organic compound chemically bonded to the silica particles via a silyloxy group, wherein the organic compound has a polymerizable unsaturated group, a group represented by the following formula (1),

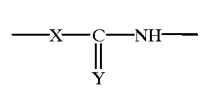

(1)

(wherein X is a group selected from —NH—, —O—, and —S— and Y is a group selected from oxygen and sulfur, provided that when X is —O—, Y is a sulfur atom), and a group represented by the following formula (2),

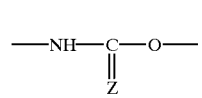

(2)

(wherein Z is a group selected from oxygen and sulfur)

Another object of the present invention is to provide a process for manufacturing reactive silica particles comprising, hydrolizing (a) a compound containing a hydrolyzable silyl group, a polymerizable unsaturated group, a group of the above formula (1), and a group of the above formula (2) in the molecule (this compound is hereinafter referred to as "hydrolyzable silane modified with a polymerizable unsaturated group") and reacting said hydrolyzed compound with (b) silica particles selected from powdery silica or colloidal silica, causing the hydrolyzable silane modified with a polymerizable unsaturated group (a) and the silica particles (b) to chemically bond together.

DETAILED DESCRIPTION OF THE INVENTION AND PREFERRED EMBODIMENTS

The process of the present invention is first illustrated, and then the reactive silica particles of the present invention will be illustrated.

Process for Manufacturing the Hydrolyzable Silane Modified with a Polymerizable Unsaturate-d Group The hydrolyzable silane modified with a polymerizable unsaturated group (a) used in the process of the present invention is characterized by comprising at least one group represented by the above formula (1), at least one group represented by the above formula (2), and at least one polymerizable unsaturated group. The hydrolyzable silyl group is a component capable of bonding to the silanol group which is present on the surface of silica particles by a hydrolysis or condensation reaction. The polymerizable unsaturated group is a component capable of crosslinking molecules by the addition reaction by the action of active radicals. The groups represented by the formula (1) or (2) are constitutional units which bind the molecules having the hydrolyzable silyl group and the molecules having the polymerizable unsaturated group directly or via other molecules. These groups are considered to provide the cured composition with excellent mechanical strength and superior characteristics such as good adhesion to substrates, heat resistance, and the like.

The hydrolyzable silyl group can for example be a carboxylate silyl groups such as an acetoxy silyl group; an alkoxy silyl group such as a methoxy or ethoxy silyl group; halogenated silyl groups such as chloro silyl group; amino silyl groups; oxime silyl groups; and hydride silyl groups. The hydrolyzable silyl group is defined as the group capable of forming a silanol group (—SiOH) by the reaction with water, optionally aided by the use of a catalyst such as for instance an acid or a base. Among the groups given above, the alkoxy silyl group is preferred.

The following groups are included in the group represented by the formula (1).

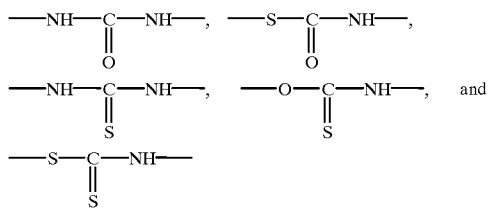

As examples of the polymerizable unsaturated group, acryloxy group, methacryloxy group, vinyl group, propenyl group, butadienyl group, styryl group, ethynyl group, cinnamoyl group, maleate group, acryl amide, and the like are given.

The compounds represented by the following formula (3) can be given as preferred examples of the hydrolyzable silane modified with a polymerizable unsaturated group (a).

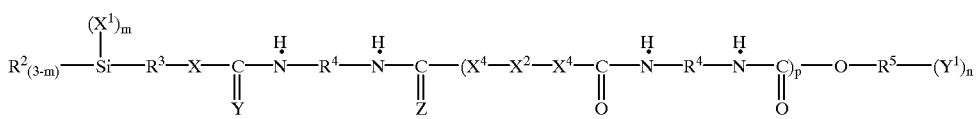

(3)

wherein $X^1$ is an alkoxy group, carboxylate group, halogen atom, amino group, oxime group or hydrogen atom; and $R^2$ represents a hydrogen atom or a monovalent organic group having 1–8 carbon atoms, such as an alkyl group, aryl group, aralkyl group, or nonhydrolyzable organic group consisting of carbon, oxygen and hydrogen atoms.

Among various groups represented by $X^1$, given as examples of the alkoxy group are methoxy, ethoxy, isopropoxy, butoxy, phenoxy, and octyloxy groups; as examples of the carboxylate group, acetoxy group; as examples of the halogen atom, iodine, chlorine, bromine, and fluorine; as examples of the amino group, monoalkyl amino groups such as amino group and methylamino group, dialkyl amino groups such as dimethylamino group and diethylamino group; and as examples of the oxime group, methylene oxime and dimethylmethylene oxime groups. m denotes 1, 2, or 3. Among these groups, the alkoxy groups are preferred.

Among various groups represented by $R^2$, given as examples of the alkyl group are methyl, ethyl, propyl, butyl and octyl groups; as examples of the aryl group, phenyl, tolyl, xylyl, and p-methoxyphenyl groups; and as examples of the aralkyl group, benzyl and phenylethyl groups; and as examples of the nonhydrolyzable organic group consisting of carbon, oxygen and hydrogen atoms, 2-methoxyethyl, 2-ethoxyethyl, and 2-butoxyethyl groups.

In the formula (3), as preferred examples of the hydrolyzable silyl group represented by the formula,

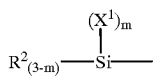

are trimethoxy silyl group, triethoxy silyl group, triisopropoxy silyl group, methyl dimethoxy silyl group, and dimethyl methoxy silyl group.

$R^3$ is selected from divalent organic groups with a $C_1$–$C_{12}$ aliphatic or aromatic structure which may include a linear, branched, or cyclic structure. Methylene, ethylene, propylene, methylethylene, butylene, methylpropylene, cyclohexylene, phenylene, 2-methylphenylene, 3-methylphenylene, octamethylene, biphenylene, dodecamethylene, and the like are given as examples of such a structural unit. Of these, methylene, propylene, cyclohexylene, and phenylene are preferred.

$R^4$ is a divalent organic group with an aliphatic or aromatic structure which may include a linear, branched, or cyclic structure. Such a structural unit may comprise 2–30 carbon atoms and be selected from the group consisting of divalent organic groups having a linear structure, such as methylene, ethylene, propylene, tetramethylene, hexamethylene, 2,2,4-trimethylhexamethylene, and 1-(methylcarboxyl)-pentamethylene; divalent organic groups having an alicyclic structure, such as isophorone, cyclohexylmethane, methylenebis(4-cyclohexane), hydrogenated diphenylmethane, hydrogenated xylene, and hydrogenated toluene; and divalent organic groups having an aromatic structure, such as benzene, toluene, xylene, p-phenylene, diphenylmethane, diphenylpropane, and naphthalene.

X is a group selected from —NH—, —O—, and —S—, preferably —S—; and Y is a group selected from oxygen atom and sulfur, preferably oxygen; provided that when X is —O—, Y is sulfur. Z is a group selected from oxygen and sulfur; Z is preferably oxygen.

$X^4$ is a group selected from —NH—, —O—, and —S— and is preferably oxygen.

$X^2$ is a divalent organic group, and more specifically, a divalent organic group derived from a compound containing in a molecule thereof at least two reactive hydrogen atoms which can react with an isocyanate group or thioisocyanate group by an addition reaction.

Examples of such a group include divalent organic groups derived from polyalkylene glycols, polyalkylene thioglycols, polyesters, polyamides, polycarbonates, polyalkylene diamines, polyalkylene dicarboxylic acids, polyalkylene diols, and polyalkylene dimercapatans by excluding two HX-groups (wherein X has the same meanings as defined above) from these groups.

p is 0, a number of 1 or higher, preferably 0 or a number of 1–10. If p is greater than 10, the viscosity of the hydrolyzable silane modified with the polymerizable unsaturated group tends to increase, making it difficult to handle the product.

$R^5$ represents an organic group with a valency of n+1, wherein n is selected from a positive integer of 1–20, preferably 1–10, and more preferably 1–5. This organic group is selected from linear, branched or cyclic saturated hydrocarbon groups, unsaturated hydrocarbon groups, and alicyclic organic groups.

$Y^1$ is a monovalent organic group containing a polymerizable unsaturated group, which is reactive to give intermolecular polymerization in the presence of active radicals. Given as examples of such a monovalent organic group are acryloxy, methacryloxy, vinyl, vinylether, vinylestes, propenyl, allylether, butadienyl, styryl, ethynyl, cinnamoyl, maleate, and acrylamide. Of these groups, acryloxy, methacryloxy, styryl and vinylether are preferred.

The structure of the hydrolyzable silane modified with the polymerizable unsaturated group used in the present invention can be obtained by a direct addition reaction of i) a hydrolyzable silane compound, ii) at least one compound selected from polyisocyanate compounds, polythioisocyanate compounds, and compounds containing both a (poly) isocyanate group and a (poly)thioisocyanate group, and iii) a polymerizable unsaturated compound containing an active hydrogen which can induce an addition reaction with the isocyanate group or thioisocyanate group.

Among the compounds of the above formula (3), the compound of the following formula (3)-1, that is, the compounds with p=0 in the formula (3), are obtained by means of this direct addition reaction.

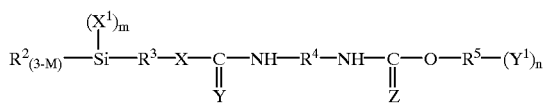

(3)-1 wherein $R^2$, $X^1$, $R^3$, X, Y, Z, $R^4$, $R^5$, $Y^1$, m, and n are the same as defined above.

The compound with a linkage

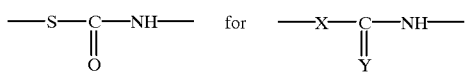

in the formula (3)-1 can be obtained, for example, by either the following process (A) or process (B):

Process (A)

The process comprising reacting an addition compound of a mercaptoalkoxy silane compound and a polyisocyanate compound to produce an intermediate compound which contains an alkoxy silyl group,

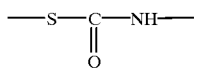

linkage group, and an isocyanate group, and then reacting the residual isocyanate of this intermediate compound with a polymerizable unsaturated compound containing an active hydrogen to link these groups via urethane bond.

Process (B)

The process comprising reacting an addition compound of a polyisocyanate compound and a polymerizable unsaturated compound containing an active hydrogen to produce an intermediate compound containing a polymerizable unsaturated group, a urethane group, and an isocyanate group, and then reacting this intermediate compound with a mercaptoalkoxy silane compound to link via the

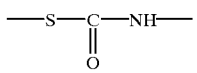

group.

The compound with a linkage

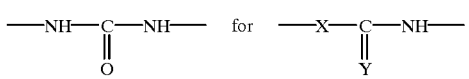

in the formula (3)-1 can be obtained by using an aminoalkoxy silane compound instead of the mercaptoalkoxy silane compound in the above process (A) or process (B).

The compound with a linkage

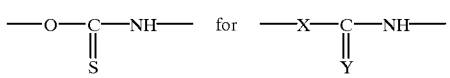

in the formula (3)-1 can be obtained by using a hydroxyalkoxy silane compound instead of the mercaptoalkoxy silane compound while using a polythioisocyanate compound instead of the polyisocyanate compound in the above process (A) or process (B). In case a polythioisocyanate compound is used, Z will by sulfur.

Further, the compound with a linkage

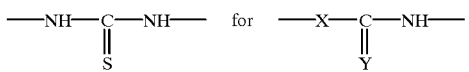

in the formula (3)-1 can be obtained by using an aminoalkoxy silane compound instead of the mercaptoalkoxy silane compound while using a polythioisocyanate compound instead of the polyisocyanate compound in the above process (A) or process (B).

Lastly, the compound with a linkage

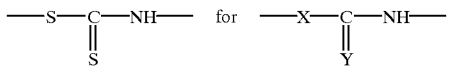

in the formula (3)-1 can be obtained by using a polythioisocyanate compound instead of the polyisocyanate compound in the above process (A) or process (B).

The processes for preparing compound of the formula (3) with p=1 will be hereinafter illustrated as processes (C) and (D).

Given as examples of the mercaptoalkoxy silane used in the processes (A) and (B) are mercaptopropyltrimethoxy silane, mercaptopropyltriethoxy silane, mercaptopropylmethyldiethoxy silane, mercaptopropyldimethoxymethyl silane, mercaptopropylmethoxydimethyl silane, mercaptopropyltriphenoxy silane, mercaptopropyltributoxy silane, and the like. Of these, mercaptopropyltrimethoxy silane and mercaptopropyltriethoxy silane are preferred. SH6062 (trademark, manufactured by Toray-Dow Corning Co.) can be given as an example of commercially available mercaptoalkoxy silane. In addition, addition compounds of aminosubstituted alkoxy silane and epoxy-substituted mercaptan, and addition compounds of epoxy silane and α,ω-dimercapto compound can be used.

Examples of the aminoalkoxy silane used in the processes (A) and (B) include aminoalkoxy silanes having a primary or secondary amino group, such as aminopropyltriethoxy silane, aminoethylaminopropyltriethoxy silane, and the like.

Examples of the hydroxyalkoxy silane used in these processes include hydroxypropyltriethoxy silane, hydroxypropyltrimethoxy silane, and the like.

The polyisocyanate compound having at least two isocyanate groups in the molecule used in these processes can be selected from organic polyisocyanate compounds with an organic structure of linear saturated hydrocarbons, cyclic saturated hydrocarbons, or aromatic hydrocarbons. The number of the isocyanate group in the molecule is usually 2–30. If more than 30, the viscosity may increase, resulting in impaired processability. A desirable range of the number of the isocyanate group is 2–10.

Given as examples of the organic polyisocyanate compounds are polyisocyanate compounds with a linear saturated hydrocarbon structure, such as tetramethylene diisocyanate, hexamethylene diisocyanate, 2,2,4-trimethylhexamethylene diisocyanate, and the like; polyisocyanate compounds with a cyclic saturated hydrocarbon structure, such as isophorone diisocyanate, dicyclohexylmethane diisocyanate, methylenebis(4-cyclohexylisocyanate), hydrogenated diphenylmethane diisocyanate, hydrogenated xylene diisocyanate, hydrogenated toluene diisocyanate, 1,3-bis(isocyanatemethyl) cyclohexane, and the like; and polyisocyanate compounds with an aromatic hydrocarbon structure, such as 2,4-toluene diisocyanate, 2,6-toluene diisocyanate, 1,3-xylene diisocyanate, 1,4-xylene diisocyanate, p-phenylene diisocyanate, 3,3'-dimethyl4,4'-diphenylmethane diisocyanate, diphenylmethane-4,4'-diisocyanate, 4,4'-biphenylene diisocyanate, 6-isopropyl-1,3-phenyl diisocyanate, 4-diphenylpropane diisocyanate, lysine diisocyanate, 1,5-naphthalene diisocyanate, polyisocyanates of polydiphenylmethane, and the like.

Among these examples, polyisocyanate compounds with a structure of alicyclic hydrocarbon or aromatic hydrocarbon are preferred. Particularly preferred are those with a structure of alicyclic hydrocarbon. Specific compounds among these preferred examples are isophorone diisocyanate, hydrogenated xylene diisocyanate, hydrogenated toluene diisocyanate, and the like. Examples of commercially available polyisocyanate compounds are TDI-80/20, TDI-100, MDI-CR100, MDI-CR300, MDI—PH, NDI (trademarks, manufactured by Mitsui-Nisso Urethane Co.), Coronate-T, Millionate MT, Millionate MR, HDI (trademarks, manufactured by Nippon Polyurethane Industries, Ltd.), Takenate 600 (trademark, manufactured by Takeda Pharmaceutical Co.), and the like.

Included in examples of the polythioisocyanate compounds used in the above processes are phenylene-p-bis (thioisocyanate), hexamethylenebis(thioisocyanate), phenylene-1-thioisocyanate-4-isocyanate, hexamethylene-1-thioisocyanate-6-isocyanate, and the like.

The amount of the polyisocyanate compounds used in the process (A) is such that the ratio of the isocyanate equivalent to the mercapto equivalent in the mercaptoalkoxy silane is usually about 0.1–100, preferably about 0.5–10, and more preferably about 0.9–1.2. If the isocyanate equivalent is less than about 0.1 of the mercapto equivalent, about 0.9 equivalent or more of mercaptosilane compounds are left unreacted. This may make abrasion resistance in the cured composition containing the reactive silica particles insufficient. The polyisocyanate compounds in an amount for which the equivalent isocyanate group exceeds 100 leaves an excess amount of unreacted isocyanate group in the product, and may impair the weather resistance in the cured composition containing the reactive silica particles.

The amount of the polyisocyanate compounds used in the process (B) is such that the ratio of the isocyanate equivalent to the equivalent of active hydrogen in the polymerizable unsaturated compounds containing the active hydrogen is about 0.1–100, preferably about 0.5–10, and more preferably about 0.9–1.2.

The above-described proportions for the amount of the polyisocyanate compounds used in the processes (A) and (B) are applicable to the amount of the polythioisocyanate compounds in the case where aminoalkoxy silane or hydroxyalkoxy silane is used instead of mercaptoalkoxy silane and polythioisocyanate compounds are used instead of the polyisocyanate compounds.

Any compounds containing at least one active hydrogen linkable with the isocyanate compound via urethane bond by the addition reaction and at least one polymerizable unsaturated group in the molecule can be used in the above processes as the polymerizable unsaturated compounds containing the active hydrogen.

Specific examples of such compounds may be, for example, polymerizable unsaturated compounds containing a carboxy group and polymerizable unsaturated compounds containing an hydroxy group. Specific examples of the polymerizable unsaturated compounds containing a carboxy group include unsaturated aliphatic carboxylic acids, such as (meth)acrylic acid, itaconic acid, cinnamic acid, maleic acid, fumaric acid, 2-(meth)acryloxypropyl hexahydro phthalate, and 2-(meth)acryloxyethyl hexahydro phthalate; unsaturated aromatic carboxylic acids, such as 2-(meth) acryloxypropyl phthalate, 2-(meth)acryloxypropylethyl phthalate; and the like. Given as specific examples of the polymerizable unsaturated compounds containing a hydroxy group are (meth)acrylate, vinyl ether or styrene compounds containing hydroxy group, such as hydroxyethyl (meth) acrylate, 2-hydroxypropyl (meth)acrylate, 2-hydroxybutyl (meth)acrylate, 2-hydroxy-3-phenyloxypropyl (meth) acrylate, 1,4-butanediol mono(meth)acrylate, 1,4-butanediol di-vinyl ether, 2-hydroxyalkyl (meth)acryloyl phosphate, 4-hydroxycyclohexyl (meth)acrylate, neopentyl glycol mono(meth)acrylate, poly(pentamethyleneoxycarboxylate) ethoxy (meth)acrylate, hydroxy styrene, hydroxy a-methylstyrene, hydroxyethyl styrene, hydroxy-terminal polyethylene glycol styryl ether, hydroxy-terminal polypropylene glycol styryl ether, hydroxy-terminal polytetramethylene glycol styryl ether, hydroxy-terminal polyethylene glycol (meth)acrylate, hydroxy-terminal polypropylene glycol (meth)acrylate, hydroxy-terminal polytetraethylene glycol (meth)acrylate, trimethylolpropane di(meth)acrylate, trimethylolpropane mono(meth)acrylate, EO-denatured trimethylolpropane tri(meth)acrylate, PO-denatured trimethylolpropane tri(meth)acrylate, pentaerythritol tri(meth) acrylate, pentaerythritol di(meth)acrylate, pentaerythritol mono(meth)acrylate, dipentaerythritol penta(meth)acrylate, dipentaerythritol tetra(meth)acrylate, dipentaerythritol tri (meth)acrylate, dipentaerythritol di(meth)acrylate, and dipentaerythritol mono(meth)acrylate.

Among these, preferred compounds are unsaturated aliphatic carboxylic acids and (meth)acrylate compounds containing hydroxy group. Particularly preferred are (meth) acrylate compounds containing hydroxy group, such as hydroxyethyl acrylate, 2-hydroxypropyl acrylate, pentaerythritol triacrylate, dipentaerythritol penta-acrylate, and the like.

The amount of the polymerizable unsaturated compounds containing the active hydrogen used, in terms of the equivalent of the active hydrogen, is usually more than about 1.0 relative to the amount of the isocyanate or thioisocyanate groups remaining in the intermediate compound obtained by the addition reaction of the alkoxy silane compound such as mercaptoalkoxy silane and the polyisocyanate or polythioisocyanate compound. If this equivalent amount of active hydrogen is less than about 1.0 (relative to the iso- or thioisocyanate groups), the resulting product contains active isocyanate or thioisocyanate groups which may react with water and cause undesirable effects such as foaming, viscosity increase, coloration, and the like.

A catalyst may be added for reducing the reaction time in either process. Either a basic catalyst or an acidic catalyst can be used as the catalyst. Examples of the basic catalyst include amines, such as pyridine, pyrrole, triethylamine, diethylamine, dibutylamine, and ammonia; and phosphines, such as tributyl phosphine and triphenyl phosphine. Of these, tertiary amines such as pyridine and triethylamine are preferred.

Given as examples of the acidic catalyst are metallic alkoxides, such as copper naphthenate, cobalt naphthenate, zinc naphthenate, DABCO, methyl DABCO, tributoxy aluminum, titanium tetrabutoxide, zirconium and tetrabutoxide; Lewis acids, such as trifluorinated boron diethyletherate and aluminum chloride; tin compounds, such as tin 2-ethylhexanoate, octyltin trilaurate, dibutyltin dilaurate, and dioctyltin diacetate.

The acidic catalysts are preferred among these, particularly tin compounds, and particularly preferably octyltin trilaurate, dibutyltin dilaurate, dioctyltin diacetate, and the like. The amount of these catalysts to be added is about 0.01–5 parts by weight, preferably about 0.1–1 part by weight, for 100 parts by weight of the polyisocyanate compounds. If this amount of the catalysts is less than about 0.01 part by weight, the effect of reducing the reaction time is only slight; if greater than about 5 parts by weight, the storage stability of the resulting product may be decreased.

To improve the flexibility and adhesiveness to substrates of the cured composition obtained from the reactive silica particles, a divalent organic group may be introduced by the addition reaction of the polyisocyanate or polythioisocyanate compound between the alkoxy silyl group and the polymerizable unsaturated group of the hydrolyzable silane modified with the polymerizable unsaturated group. A linear, branched, or cyclic organic compound containing at least two active hydrogens in the molecule capable of reacting with the polyisocyanate or polythioisocyanate group by the addition reaction can be used as a precursor of such a divalent organic group. In this instance, the compound of said formula (3) with p=1 or larger is produced.

Hydroxy group, carboxy group, mercapto group, amino group, sulfonic acid group, phosphoric acid group, silanol group, and the like can be given as examples of the group which can provide the active hydrogen. The compounds has preferably 2–10, and more preferably two active hydrogens in the molecule. The number average molecular weight of the compounds which contain the active hydrogen is usually about 50–100,000, preferably about 100–50,000, and more preferably about 500–10,000.

As examples of the compound which gives such a divalent organic group, polyalkylene glycols, polyalkylene thioglycols, polyester diols, polyamides, polycarbonate diols, polyalkylene diamines, polyalkylene dicarboxylic acids, polyalkylene diols, polyalkylene dimercaptans, and the like are given. Polyalkylene glycols are preferred among these compounds. The polyalkylene glycols can be selected from commercially available polyalkylene glycols, such as polyethylene glycol, polypropylene glycol, polytetraethylene glycol, and polyhexamethylene glycol, or copolymers of two or more of these polyalkylene glycols. Specific examples of commercially available products include Unisafe DC1100, Unisafe DC1800, Unisafe DCB1100, Unisafe DCB1800 (trademarks, manufactured by Nippon Oil and Fats Co., Ltd.), PPTG 4000, PPTG 2000, PPTG 1000, PTG 2000, PTG 3000, PTG 650, PTGL 2000, PTGL 1000 (trademarks, manufactured by Hodogaya Chemical Co., Ltd.), EXCENOL 1020 (trademark, manufactured by Asahi Glass Co., Ltd.), and PBG 3000, PBG 2000, PBG 1000, Z 3001 (trademarks, manufactured by Daiichi Kogyo Seiyaku Co., Ltd.).

Now, the processes for manufacturing the hydrolyzable silane modified with the polymerizable unsaturated group which contains these compounds as constitution units are illustrated by taking polyalkylene glycol as an example.

Process (C)

Polyalkylene glycol is added to an addition compound having an active isocyanate group at the terminal thereof, made from a mercaptoalkoxy silane and a polyisocyanate compound, to produce an alkoxy silane with a hydroxy group at the terminals. This compound is reacted with an addition compound having a hydroxy group at the terminal which is separately made from a polymerizable unsaturated compound and a polyisocyanate compound, to link these two compounds with a urethane bond.

Process (D)

The addition compound having an active isocyanate group at the terminal, made from a mercaptoalkoxy silane and a polyisocyanate compound, is reacted with the addition compound having an active hydrogen at the terminal thereof, which is separately made from a polyalkylene glycol-polyisocyanate compound and a polymerizable unsaturated compound with a hydroxy group, to link these addition compounds with a urethane bond.

The conditions for forming the urethane bond used in the processes (C) and (D) are the same as those in the processes (A) and (B), and the equivalent ratio of groups involved in the linkage, that is, the ratio of the compound having the active isocyanate group in the terminal to the compound having hydroxy group at the terminal is usually in the range of about 1.0–1.2. If this ratio is smaller than about 1.0, the resulting product tends to be colored or its viscosity tends to increase.

The modifications of processes (A) and (B) illustrated above for the cases where aminoalkoxy silane or hydroxyalkoxy silane is used instead of mercaptoalkoxy silane and polythioisocyanate compounds are used instead of the polyisocyanate compounds are applicable to the processes (C) and (D).

Process for Manufacturing Reactive Silica Particles

Silica particles (b), another raw material used in the process of the present invention, are in general powdery or colloidal silica particles. Silica particles having an average diameter of about 0.001–20 $\mu$m are preferably used. When transparant films of the cured material using the reactive silica particles of the present invention are intended, the average diameter is preferably about 0.001–2 $\mu$m, more preferably about 0.001–0.1 $\mu$m, and particularly preferably about 0.001–0.01 $\mu$m. Regarding the shape, the silica particles may be selected from spherical, hollow, porous, rod, plate, or fibrous silica particles or amorphous silica powder, preferably from spherical silica particles. The specific surface area of the silica particles is preferably about 0.1–3,000 $m^2/g$, and more preferably about 10–1,500 $m^2/g$. These silica particles can be used as dry powder or particles, or dispersed in an organic solvent. It is possible to use a dispersion of fine particles of silica—known as colloidal silica in the art—as is. The use of the colloidal silica is particularly preferred when transparency of films is pursued.

When the dispersion medium for colloidal silica is water, acidic colloidal silica with a pH in the range of 2–10, preferably in the range of 3–7, is preferred. When the dispersion medium for colloidal silica is an organic solvent, the organic solvent is preferably selected from methanol, isopropanol, ethylene glycol, butanol, ethylene glycol monopropyl ether, methyl ethyl ketone, methyl isobutyl ketone, toluene, xylene, dimethylformamide, and the like, and mixtures of two or more of these solvents, mixtures of these solvents and other solvents which are mutually soluble with these solvents, and mixtures of these solvents and water. Among these solvents, methanol, isopropanol, methyl ethyl ketone, and xylene are preferred.

Commercially available silica particles which can be used include colloidal silica, such as methanol silica sol, IPA—ST, MEK—ST, NBA—ST, XBA—ST, DMAC—ST, ST—UP, STOUP, ST-20, ST-40, ST—C, ST—N, ST-0, ST-50, ST—OL (trademarks, all manufactured by Nissan Chemical Co.); powdery silica, such as AEROSIL 130, AEROSIL 300, AEROSIL 380, AEROSIL TT600, AEROSIL OXSO (trademarks, manufactured by AEROSIL Co.), Sildex H31, H32, H51, H52, H121, H122 (trademarks, manufactured by Asahi Glass Co.), E220A, E220 (trademarks, manufactured by Nippon Silica Industries), SYLYSIA 470 (trademark, all manufactured by Fuji Sylysia Co.), SG-Flake (trademark, all manufactured by Nippon Sheet Glass Co.), and the like.

The reactive silica partiacles can be made in several different ways. The hydrolyzable silane (a) and the silica particles (b) for example can be chemically combined by mixing the hydrolyzable silane modified with the polymerizable unsaturated group (a) and silica particles (b) and by subjecting the mixture to hydrolysis according to the process of the present invention. The proportion of polymerized organic components in the resulting reactive silica particles, that is, the proportion of hydrolyzate and condensate of the hydrolyzable silane, can be determined as the weight reduction (%) when the dry powder is completely combusted in the air, for example, by the thermogravimetric analysis in the air at a temperature usually from room temperature to 800° C.

Regarding the ratio of the hydrolyzable silane modified with the polymerizable unsaturated group (a) and silica particles (b) used in the present invention, about 0.01–100 parts by weight of silica particles or colloidal silica (b), on dry basis, is preferably used for 1 part by weight of the hydrolyzable silane modified with the polymerizable unsaturated group (a). If this ratio of the component (b) for 1 part by weight of the component (a) is less than about 0.01 part by weight or greater than about 100 parts by weight, the effects of the present invention are exhibited only slightly.

An amount of water to hydrolyze at least one hydrolyzable group present on one silicon element is sufficient to cause a reaction between the hydrolyzable silane and the silica particles(a). Preferably, the amount of water present or added when the hydrolysis is carried out is at least about ⅓, more preferably at least about ½, but less than about 3 times, relative to the total number of mol of hydrolyzable groups ($X^1$) present on the silicon. The product obtained by mixing the hydrolyzable silica modified with polymerizable unsaturated group (a) and silica particles (b) in the complete absence of water is a product in which the hydrolyzable silica modified with polymerizable unsaturated group is physically attached to the surface of silica particles. Only poor abrasion resistance is exhibited by the cured materials produced from such a product.

As the hydrolyzate of the hydrolyzable silane modified with polymerizable unsaturated group, it is possible to use a co-hydrolyzate with other organic alkoxy silane, e.g. a co-condensate with an alkoxy silane such as tetramethoxy silane, tetraethoxy silane, tetrabutoxy silane, methyltrimethoxy silane, methyltriethoxy silane, dimethyldimethoxy silane, or phenylmethoxy silane. When the co-hydrolyzate is manufactured, the amount of water used for the hydrolysis is usually about 0.5–1.5 times the amount of all alkoxy groups. The co-hydrolyzate or co-condensate can be obtained by stirring the mixture at 0° C. to the boiling point of the components for 5 minutes to 24 hours in the presence or absence of water. An acidic or basic catalyst can be used for reducing the reaction time.

The reactive silica particles of the present invention can be manufactured by a process comprising independently hydrolyzing the hydrolyzable silane modified with polymerizable unsaturated group (a), then mixing the hydrolyzate with silica particles (b), and heating and stirring the mixture; a process comprising the hydrolysis of the hydrolyzable silane modified with polymerizable unsaturated group (a) in the presence of silica particles (b); or a process comprising a treatment the surface of the silica particles (b) in the presence of a polyvalent unsaturated organic compound, a monovalent unsaturated organic compound, or a radiation sensitive initiator. The process carrying out the hydrolysis of the hydrolyzable silane modified with polymerizable unsaturated group (a) in the presence of silica particles (b) is preferred. The manufacture of the reactive silica particles is preferably carried out at 20–150° C. and the treating time is preferably in the range of 5 minutes to 24 hours.

The silica particles used in the present invention are known to contain adsorbed water on the particle surface under normal conditions of storage or as provided as a product. For example, a colloidal silica product dispersed in an organic solvent usually contains about 0.5 wt. % of water. Therefore, it is possible to utilize this water contained in the raw material when manufacturing the reactive silica particles of the present invention by simply mixing the hydrolyzable silane modified with polymerizable unsaturated group (a) and the silica particles (b) and subjecting the mixture to a heating and stirring treatment. It is also possible to manufacture the reactive silica particles by blending the hydrolyzable silane modified with polymerizable unsaturated group (a), the silica particles (b), and a monovalent or polyvalent unsaturated polymerizable organic compound in the presence of water or an organic solvent, then removing the water or an organic solvent from the mixture under reduced or atmospheric pressure.

In the manufacture of the reactive silica particles of the present invention, especially, when powdery silica particles are used as the silica particles (b), it is possible to add an organic solvent mutually soluble with water to effect a smooth and homogeneous reaction of the group (a) and the silica particles (b). Alcohols, ketones, ethers, and amides are given as the solvent suitably used for this purpose. Specific examples of such organic solvents include alcohols, such as methanol, ethanol, isopropanol, butanol, ethylene glycol monomethyl ether, and ethylene glycol monobutyl ether; ketones, such as acetone, methyl ethyl ketone, and methyl isobutyl ketone; and amides, such as dimethylformamide, dimethylacetamide, N-methylpyrrolidone, and γ-butyrolactone. There are no specific limitations to the amount of these solvents to be added to ensure a smooth and homogeneous reaction.

It is possible to add an acid, a salt, or a base as a catalyst to accelerate the reaction in the manufacture of the reactive silica particles. Given as examples of the acid are inorganic acids, such as hydrochloric acid, nitric acid, sulfuric acid, and phosphoric acid; organic acids, such as methane sulfonic acid, toluene sulfonic acid, phthalic acid, malonic acid, formic acid, acetic acid, and oxalic acid; and unsaturated organic acids, such as methacrylic acid, acrylic acid, and itaconic acid. Ammonium salts such as tetramethyl ammonium chloride, tetrabutyl ammonium chloride, and the like can be given as examples of the salt. Examples of the base include ammonia water; primary, secondary, or tertiary aliphatic amines such as diethylamine, triethylamine, dibutylamine, and cyclohexylamine; aromatic amines such as pyridine; sodium or potassium hydroxide; quarternary ammonium hydroxides, such as methyl ammonium hydroxide, tetrabutyl ammonium hydroxide, and the like. Preferred catalysts among these are organic acids, unsaturated organic acids, tertiary amines, and quarternary ammonium hydroxides. The amount of the acid or base catalyst to be added is about 0.001–1.0% by weight, preferably about 0.01–0.1% by weight, of the amount of the hydrolyzable silane modified with polymerizable unsaturated group.

Reactive silica particles

The reactive silica particles can be manufactured by means of the above described process according to the present invention.

As can be understood from the above descriptions, in the reactive silica particles of the present invention the compound (a) containing a hydrolyzable silyl group, a polymerizable unsaturated group, a group of the above formula (1), and a group of the above formula (2) in the molecule (the hydrolyzable silane having a polymerizable unsaturated group) is chemically linked to silica particles (b), i.e. powdery silica or colloidal silica, via a silyloxy group.

Specifically, the hydrolyzable silyl groups in the compound (a) form silyloxy groups between the silica particles by hydrolysis to chemically bond and fix to the silica particles.

The amount of the hydrolyzable silane modified with polymerizable unsaturated group fixed to the reactive silica particles is about 0.05–99% by weight, and preferably about 5–85% by weight. If the amount fixed is less than about 0.05% by weight, the effects on scratch resistance and transparency of the cured product made from the coating composition is insufficient; if this is greater than about 99% by weight, improvement in the scratch resistance of the cured product is only slight.

Curable composition containing reactive silica particles

A curable composition comprising the reactive silica particles and optionally a compound containing at least one polymerizable unsaturated group is provided by the present invention. Either polyunsaturated organic compounds containing two or more polymerizable unsaturated groups and/or monounsaturated organic compounds containing one polymerizable unsaturated group can be used as the polymerizable unsaturated compound.

The amount of the polyunsaturated organic compounds is usually about 0–2,000 parts by weight, preferably about 10–1,000 parts by weight, and more preferably about 100–800 parts by weight, for 100 parts by weight of the reactive silica particles in the composition. If this amount is less than about 10 parts by weight, there is a tendency for the curability to be decreased; if greater than about 2,000 parts by weight, there is a tendency for the coatability to be decreased. The amount of the mono-unsaturated organic compounds is usually about 0–1,000 parts by weight, and more preferably about 10–500 parts by weight, for 100 parts by weight of the reactive silica particles in the composition.

If this amount is greater than about 1,000 parts by weight, there is a tendency for the coatability to be decreased.

The polyunsaturated organic compound that preferably is used in the present invention is a polyunsaturated organic compound containing two or more polymerizable unsaturated groups in the molecule. Such a compound is selected from organic compounds having an aliphatic or aromatic skeleton containing at least two groups selected from (meth) acryloxy group, vinyl group, or styryl group, wherein the aliphatic or aromatic skeleton may contain other units such as (linear, branched, or cyclic) ester, urethane, ether, and the like. Polyfunctional urethane (meth)acrylates of the following formula (4) can be given as examples of the unsaturated organic compounds containing the urethane bond.

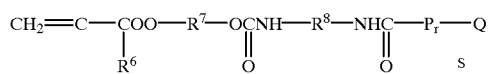

$$CH_2{=}C{-}COO{-}R^7{-}OCNH{-}R^8{-}NHC{-}P_r{-}Q \atop {\phantom{CH_2{=}C{-}}R^6 \phantom{{-}COO{-}R^7{-}}O \phantom{CNH{-}R^8{-}N}O \phantom{HC{-}P_r{-}}s}}$$

wherein $R^6$ is a hydrogen atom or a methyl group; $R^7$ is a divalent hydrocarbon group having 2–100 carbon atoms which may contain ether bonds, carboxylate bonds, or phosphate bonds; Re represents a diisocyanate residue; P represents the group of the following formula (5), $$-Z^1-CONH-R^8-NHCO- \qquad (5)$$

(wherein $Z^1$ is a polymer diol residue and $R^8$ is the same as defined above); Q is a polyhydric alcohol residue; s is an integer of 2–6; and r is an integer of 0–3. The polymer diol residue represented by $Z^1$ in the formula (5) includes polyether diol residue, polyester diol residue, polycaprolactone diol residue, polymethylvalerolactone diol residue, polycarbonate diol residue, and the like.

This type of polyfunctional urethane (meth)acrylates can be prepared, for example, by reacting a polyisocyanate compound, a (meth)acrylate compound having a hydroxy group at the terminal, and a polyhydric alcohol. These polyfunctional urethane (meth)acrylates are commercially available under the trademarks of KAYARAD-UX2201, -UX2301, -UX3204, -UX3301, -UX4101, -UX6101, -UX7101, -UX 8101 (manufactured by Nippon Kayaku Co., Ltd.), and the like. As examples of the unsaturated organic compounds containing the ester binding unit, acrylmodified epoxy resins available from Nippon Kayaku Co., Ltd. under the trademarks of KAYARAD-R-011, -R-300, -R130, -R190, -EX2320, -R205, -R131, -R146, and -R280 and polyester acrylates also available from Nippon Kayaku Co., Ltd. under the trademarks of KAYARAD-PAR100 and -PAR300, are given.

In addition to these compounds, the following compounds are given as examples of the polyunsaturated organic compound: dipentaerythritol hexa(meth)acrylate, trimethylolpropane (meth)acrylate, pentaerythritol tri(meth)acrylate, ethylene glycol di(meth)acrylate, triethylene glycol divinyl ether, tetraethylene glycol (meth)acrylate, tripropylene glycol (meth)acrylate, 1,4—butanediol di(meth)acrylate, 1,6-hexanediol di(meth)acrylate, neopentyl glycol di(meth) acrylate, trimethylolpropane trioxyethyl (meth)acrylate, tris (2—hydroxyethyl)isocyanurate tri(meth)acrylate, tricyclodecanedimethanol di(meth)acrylate, epoxy (meth) acrylates obtained by the addition of (meth)acrylate to a diglycidyl ether such as bisphenol A. Examples of commercially available products which can be used are YUPIMER-UV, SA1002, SA2007 (manufactured by Mitsubishi Chemical Co.), Viscoat 700, Viscoat 2150 (manufactured by Osaka Organic Chemical Industry Ltd.), KAYARAD-HDDA, -NPGDA, -TPGDA, -PEG400DA, -MANDA, -R526, -HBA-240P, -R551, -R684, -GPO303, -R712, -R604, -R167, -TMPTA, -TPA320, -TPA330, -PET30, -DCPA20, -DCPA30, -DCPA60, -DCPA120, -HX220, -HX620, -D310, -D330, DPHA, KAYAMER-PM1, -PM2, -PM21 (manufactured by Nippon Kayaku Co.), and the like.

The monounsaturated organic compound used in the present invention is a compound containing one polymerizable unsaturated group in the molecule. Preferably, such a compound is an organic compound having an aliphatic or aromatic skeleton and containing one group selected from (meth)acryloxy group, vinyl group, or styryl group, therein the aliphatic or aromatic skeleton may contain monovalent organic group or a divalent linking unit such as (linear, branched, or cyclic) ester, urethane, ether, alkylene, phenylene, and the like.

The following compounds are given as examples of the mono-unsaturated organic compound: neutral (meth) acrylates and aromatic vinyl compounds, such as 2-hydroxyethyl (meth)acrylate, 2-hydroxypropyl (meth) acrylate, 2-hydroxybutyl (meth)acrylate, methyl (meth) acrylate, ethyl (meth)acrylate, propyl (meth)acrylate, butyl (meth)acrylate, phenyl(meth)acrylate, 2-ethylhexyl (meth) acrylate, cyclohexyl (meth)acrylate, amyl (meth)acrylate, pentyl (meth)acrylate, octyl (meth)acrylate, lauryl (meth) acrylate, stearyl (meth)acrylate, tetrahydrofurfuryl (meth) acrylate, butoxyethyl (meth)acrylate, benzyl (meth)acrylate, ethoxydiethylene glycol (meth)acrylate, phenoxyethyl (meth)acrylate, polyethylene glycol (meth)acrylate, polypropylene glycol (meth)acrylate, methoxypolypropylene glycol (meth)acrylate, methoxypolyethylene glycol (meth)acrylate, dicyclopentenyl (meth)acrylate, tricyclodecanyl (meth)acrylate, bornyl (meth)acrylate, isobornyl (meth)acrylate, diacetone (meth)acrylamide, isobutoxymethyl (meth)acrylamide, γ-vinyl caprolactone, styrene, α-methylstyrene, allylphthalate, diallylphthalate, (meth) acrylamide, and the like; acidic (meth)acrylates, such as (meth)acrylic acid, itaconic acid, 2-(meth)acryloxypropyl phthalate, and 2-(meth)acryloxypropylhexahydrogen phthalate; and basic (meth)acrylates, such as dimethylaminopropyl (meth)acrylate, and (meth)acryloyl morpholine; basic vinyl compounds, such as vinyl pyridine and vinyl pyrrolidone; and the like. Of these, neutral (meth)acrylates, acidic (meth)acrylates, and basic (meth)acrylates are preferred.

The composition of the present invention is cured by heat and/or radiation. Electric heaters, infrared lamps, hot air, and the like can be used as the source of heating. Here, the radiation means radiations such as infrared lights, visible lights, ultraviolet lights, X-rays, electron beams, α-rays, β-rays, and γ-rays. There are no limitations to the source of these radiations insofar as the object of curing the composition can be achieved in a short period of time after coating. Specific examples of such radiation sources include infrared light sources, such as lamps, resistance heating plates, and laser; visible light sources, such as sunlights, lamps, fluorescent lights, and laser; UV light sources, such as mercury lamps, halide lamps, and laser. A method of utilizing thermions emitted from a commercially available tungsten filament, a cold cathodic method generating electron beams by passing a high voltage pulse through a metal, and a secondary electron method utilizing secondary electrons generated by collision of ionized gaseous molecules and a metallic electrode are used as the sources of electron beams. Substances such as $Co^{60}$ and the like can be used as the source of generating α-rays, β-rays, and γ-rays. In addition, a vacuum tube of the type colliding accelerated electrons against the anode can be used to generate γ-rays. These radiations can be used either individually or in combination of two or more sources. In addition, it is possible to irradiate two or more radiations separately at a prescribed interval. A polymerization initiator may be added to the composition of the present invention to reduce the curing time. The compounds capable of producing activation radicals either by heating or radiation can be used as the polymerization initiator.

Given as examples of the polymerization initiator generating activation radicals by heat are peroxides, such as hydroxy peroxides and dialkyl peroxides, and azo compounds. Specific examples include peroxides, such as tert-butylhydroperoxide, cumyl peroxide, benzoyl peroxide, m-chlorobenzoyl peroxide, and peracetate; azobisisobutyronitrile, azobisvaleronitrile, and the like.

The polymerization initiator generating activation radicals by heat is preferably added immediately before the curing treatment, usually, in an amount of about 0.1–2 parts for 100 parts of the curable composition.

The polymerization initiator generating activation radicals by radiation (hereinafter referred to as photoinitiator) is preferably selected from the compounds which generate activation radicals by irradiation of UV lights. The photoinitiator is added to the composition in an amount of about 0.1–10 parts by weight, preferably about 1–5 parts by weight, for 100 parts by weight of solid components in the curable composition. The curing speed is slow when this amount is less than about 0.1 part by weight, whereas the amount exceeding about 10 parts by weight is uneconomical.

Given as examples of the photoinitiator are 1-hydroxycyclohexyl phenyl ketone, 2,2-dimethoxy-2-phenyl acetophenone, xanthone, fluorenone, benzaldehyde, fluorene, anthraquinone, triphenylamine, carbasole, 3-methylacetophenone, 4-chloroacetophenone, 4,4'-dimethoxyacetophenone, 4,4'-diaminobenzophenone, Michler's ketone, benzoin propyl ether, benzoin ethyl ether, benzyl dimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholinopropan-1-one, 2,4, 6-trimethylbenzoyldiphenylphosphine oxide, and the like, and commercially available products, such as IRGACURE 184, 651, 500, 907, CGI1369, CG24–61 (trademarks, manufactured by Ciba Geigy); LUCIRINE LR8728 (trademark, manufactured by BASF); Darocure 1116, 1173 (trademarks, manufactured by Merck Co.); Uvecryl P36 (trademark, manufactured by UCB Co.); VICURE 55 (trademark, manufactured by AKZO Co.); and the like.

A photosensitizer can be used together with photoinitiators. Given as examples of the photosensitizer are triethylamine, diethylamine, N-methyldiethanolamine, ethanolamine, 4-dimethylamino-benzoic acid, isoamyl 4-dimethylaminobenzoate, and commercially available products such as Uvecryl P102, P103, P104, and P105 (trademarks, all manufactured by UCB Co.). The photosensitizer is used in an amount usually in the range of 1–500 parts by weight for 100 parts by weight of the photoinitiator.

A dehydrating agent selected from ortho-esters of an organic carboxylic acid and a ketal may be added to the composition of the present invention. The first object of the addition of dehydrating agent is to extend the storage stability of the composition without impairing the characteristics of the cured products. These dehydrating agents are added to prevent formation of undesirable agglomerated products due to hydrolysis or condensation of unreacted alkoxy silyl groups contained in the composition. The second object is to accelerate formation of chemical bonds of hydrolyzable silane modified with polymerizable unsaturated groups to the silica particles. Examples of the ortho-esters of an organic carboxylic acid and a ketal used in the present invention include methyl ortho-formate, ethyl ortho-formate, methyl ortho-acetate, ethyl ortho-acetate, acetone dimethyl ketal, diethyl ketone dimethyl ketal, acetophenone dimethyl ketal, cyclohexanone dimethyl ketal, cyclohexanone diethyl ketal, benzophenone dimethyl ketal, and the like. Of these, the ortho-esters of an organic carboxylic acid, particularly methyl ortho-formate and ethyl ortho-formate, are preferred. These dehydrating agents may be added to the composition of the present invention in an amount of 1–10 mols, preferably 1–3 mols, for 1 mol of water contained in the composition. If the amount of the dehydrating agent is less than one mol, improvement in the storage stability may be insufficient. These dehydrating agents are preferably added after the composition has been formulated, thereby improving the storage stability of the composition and accelerating formation of the chemical bonds between the hydrolyzable silane modified with polymerizable unsaturated groups and the silica particles.

Beside the above components, the composition of the present invention may be formulated with various components, as required, such as antioxidants, UV absorbers, photo-stabilizers, thermal polymerization inhibitors, leveling agents, surfactants, lubricants, solvents, and the like. Commercially available antioxidants, which can be used are Irganox 1010, 1035, 1076, 1222 (manufactured by Ciba Geigy), and the like. As UV absorbers Tinuvin P234, P320, P326, P327, P328, P213, P329 (manufactured by Ciba Geigy), Seesorb 102, 103, 501, 202, 712, (manufactured by Sypro Chemical Co.), and the like are given as examples. Commercially available photo-stabilizers which can be added include Tinuvin 292, 144, 622LD (manufactured by Ciba Geigy), Sanol LS770, LS440 (manufactured by Sankyo Chemical Co.), and SUMISORB TMO61 (manufactured by Sumitomo Chemical Industries).

The composition of the present invention has a viscosity usually of 5–20,000 cp/25° C., and preferably 10–10,000 cp/25° C.

The composition of the present invention is ideal as a coating agent. The substrates to which the composition is applied with advantage include plastics, metals, wood, papers, glasses, slates, and the like, with preferred materials being plastics, wood, and papers. Examples of the plastics used together with the composition of the present invention include plastic molded materials made from polycarbonate, polyacrylate, polyester, polyvinyl chloride, polyamide, polyimide, polypropylene, polyethylene, or the like, particularly preferably polycarbonate, polyacrylate, polyvinyl chloride, or polyester. The substrates to be coated may be of any shape, such as plates, films, or three-dimentional objects. Common methods of coating, such as dipping, spraying, flow coating, shower coating, roll coating, coating with a brush, and the like are applicable as the method for coating. The thickness of the coating is usually about 0.1–400 μm, and preferably about 1–200 μm, in particular about 5–100 μm.

After coating, the composition is dried by evaporating volatile matters at a temperature of 0–200° C., preferably about 10–100° C., for 1 seconds to 72 hours, preferably for 5 seconds to 24 hours, and more preferably for 5 seconds to 1 hour. After drying, the composition is cured by heat and/or radiation to obtain molded articles with coating. The curing is preferably carried out at a temperature of 20–150° C. for 10 seconds to 1 hour. UV light or electron beam is preferably used as a radiation source for curing the composition of the present invention by radiation. In this instance, the quantity of UV light irradiated is in the range of about 0.01–10 J/cm², and preferably about 0.1–2 J/cm². Preferable irradiation conditions of electron beam is 10–300 KV and 0.02–0.30 mA/cm² with the amount of electron beam of about 1–10 Mrad.

EXAMPLES

The present invention will be illustrated in more detail by way of examples which are given for illustration purpose only and are not intended to be limiting of the present invention. In the examples below "part (or parts) by weight" is simply referred to as "part (or parts)".

Preparation of hydrolyzable silane with polymerizable unsaturated groups

Reference Example 1

223 parts of 1,3-bis(isocyanatemethyl)-cyclohexane was added dropwise to a solution of 221 parts of mercaptopropyltrimethoxy silane and 1 part of dibutyltin dilaurate while stirring in dry air at 50° C. over 1 hour, followed by stirring at 70° C. for 3 hours. Then, 555 parts of pentaerythritol triacrylate was added at 30° C. over 1 hour, and the mixture was stirred at 60° C. for 10 hours while stirring to obtain silane compound A. Analysis of residual isocyanate in the resulting product revealed that the amount was 0.1% or lower, indicating that the reaction completed almost quantitatively. The IR spectrum of this product confirmed that the peaks at 2,550 and 2,260 kaysers characteristic respectively to mercapto groups and isocyanate groups in the raw material have disappeared, and a peak at 1,660 kayser characteristic to urethane bond and

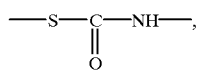

and a peak at 1,720 characteristic to acryloxy group have newly appeared, indicating the production of an alkoxy silane modified with acryloxy group, which has both the acryloxy group and the group

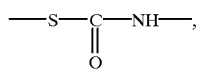

as polymerizable unsaturated groups, and the urethane bond.

Reference Example 2

223 parts of 1,3-bis(isocyanatemethyl)-cyclohexane was added dropwise to a solution of 221 parts of mercaptopropyltrimethoxy silane and 1 part of dibutyltin dilaurate while stirring in dry air at 50° C. over 1 hour, followed by stirring at 70° C. for 3 hours. Then, 131 parts of hydroxyethyl acrylate was added at 30° C. over 1 hour, and the mixture was stirred at 60° C. for 10 hours while stirring to obtain silane compound B. Analysis of residual isocyanate in the resulting product revealed that the amount was 0.1% or lower, indicating that the reaction completed almost quantitatively.

Reference Example 3

115 parts of 1,3-bis(isocyanatemethyl)-cyclohexane was added dropwise to a vessel (vessel 1) which contained a solution of 114 parts of mercaptopropyltrimethoxy silane and 1 part of dibutyltin dilaurate hile stirring in dry air at 50° C. over 1 hour, and the mixture was stirred at 70° C. for 3 hours. In another vessel (vessel 2), 67 parts of hydroxyethyl acrylate was added dropwise to a solution of 114 parts of 1,3-bis(isocyanatemethyl)cyclohexane, 1 part of dibutyltin dilaurate, and 2 part tert-butylhydroquinone while stirring in dry air at 50° C. over 0.5 hour, and the mixture was stirred at 50° C. for 3 hours. 588 parts of poytetramethylene glycol having an average molecular weight of 1,000 was added to the mixture, followed by stirring at 50° C. for 3 hours. Then, the mixture of vessel 2 was added dropwise to vessel 1 at 30° C. over 1 hour, and the resulting mixture was stirred at 50° C. for 6 hours while stirring to obtain silane compound C.

Analysis of residual isocyanate in the resulting product revealed that the amount was 0.1% or lower, indicating that the reaction completed almost quantitatively.

Preparation of reactive silica particles

The reactive silica particles shown in Table 1 were prepared in the following Examples.

Example 1

A mixture of 30 parts of silane (A) prepared in Reference Example 1, 233 parts of colloidal silica dispersed in methyl ethyl ketone (average particle size: 0.01–0.015 μm, silica concentration: 30%; MEK—ST: trademark, manufactured by Nissan Chemical Co.), 5 parts of isopropanol,.and 3 parts of ion-exchanged water was stirred for 3 hours at 80° C. under a dry nitrogen stream. After the addition of 18 parts of methyl ortho-formate, the mixture was stirred for a further 1 hour at the same temperature to produce a colorless, transparant dispersion (dispersion 1a).

Example 2

A mixture of 80 parts of silane (A) prepared in Reference Example 1, 20 parts of silica powder (average particle size: 0.04 μm; AEROSIL TT600: trademark, manufactured by AEROSIL Co.), 5 parts of isopropanol, 47 parts of ethyl acetate, and 7 parts of ion-exchanged water was vigorously stirred for 3 hours at 80° C. under a dry nitrogen stream. After the addition of 41 parts of methyl ortho-formate, the mixture was stirred for a further 1 hour at the same temperature to produce a semitransparent dispersion (dispersion 1b).

Example 3

A mixture of 30 parts of silane (A) prepared in Reference Example 1, 70 parts of silica powder (average particle size: 1 μm; Nipseal E220A: trademark, manufactured by Nippon Silica Industries), 5 parts of isopropanol, 74 parts of ethyl acetate, and 3 parts of ion-exchanged water was stirred for 3 hours at 80° C. under a dry nitrogen stream. After the addition of 18 parts of methyl ortho-formate, the mixture was stirred for a further 1 hour at the same temperature to produce a semi-transparent dispersion (dispersion 1c).

Example 4

A mixture of 30 parts of silane (A) prepared in Reference Example 1, 70 parts of silica powder (average particle size: 12 μm; Sildex H122: trademark, manufactured by Asahi Glass Co.), 5 parts of isopropanol, 74 parts of ethyl acetate, and 3 parts of ion-exchanged water was vigorously stirred for 3 hours at 80° C. under a dry nitrogen stream. After the addition of 18 parts of methyl ortho-formate, the mixture was stirred for a further 1 hour at the same temperature to produce a semitransparent dispersion (dispersion 1d).

Example 5

A mixture of 78 parts of silane (B) prepared in Reference Example 2, 865 parts of MEK—ST, and 8 parts of ion-exchanged water was stirred for 3 hours at 80° C. under a dry nitrogen stream. After the addition of 49 parts of methyl ortho-formate, the mixture was stirred for a further 1 hour at the same temperature to produce a semi-transparent dispersion (dispersion 1e).

Example 6

A mixture of 81 parts of silane (C) prepared in Reference Example 3, 900 parts of MEK—ST, and 3 parts of ion-exchanged water was stirred for 3 hours at 80° C. under a dry nitrogen stream. After the addition of 15 parts of methyl ortho-formate, the mixture was stirred for a further 1 hour at the same temperature to produce a semi-transparent dispersion (dispersion 1f).

Example 7

A mixture of 80 parts of silane (A) prepared in Reference Example 1, 67 parts of MEK—ST, and 7 parts of ion-exchanged water was stirred for 3 hours at 80° C. under a dry nitrogen stream. The mixture was stirred for a further 1 hour at the same temperature to produce a semi-transparent dispersion (dispersion 1g).

TABLE 1

| Reactive silica particles | 1a | 1b | 1c | 1d | 1e | 1f | 1g |
|---|---|---|---|---|---|---|---|
| Silane compound | | | | | | | (parts by weight) |
| A | 30 | 80 | 30 | 30 | — | — | 80 |
| B | — | — | — | — | 78 | — | — |
| C | — | — | — | — | — | 81 | — |
| Silica particles | | | | | | | |
| MEK-ST | 233 | — | — | — | 865 | 901 | 67 |
| AEROSIL TT600 | — | 20 | — | — | — | — | — |
| Nipseal E220A | — | — | 70 | — | — | — | — |
| Sildex H122 | — | — | — | 70 | — | — | — |
| Ion-exchanged water | 3 | 7 | 3 | 3 | 8 | 3 | 7 |
| Isopropanol | 5 | 5 | 5 | 5 | — | — | — |
| Ethyl acetate | — | 47 | 74 | 74 | — | — | — |
| Metyl ortho-formate | 18 | 41 | 18 | 18 | 49 | 15 | — |
| Total | 289 | 200 | 200 | 200 | 1000 | 1000 | 154 |
| Solid component concentration (%) | 37 | 50 | 50 | 50 | 34 | 35 | 65 |
| Silica concentration in solid component (%) | 70 | 20 | 70 | 70 | 77 | 77 | 20 |

Preparation of compositions

The compositions, of which the formulations of the components are shown in Table 2, were prepared in the following Examples.

Example 8

A mixture of 520 parts of the dispersion 1a prepared in Example 1, 400 parts of dipentaerythritol hexaacrylate (manufactured by Nippon Kayaku Co.), 100 parts of 2-acryloxypropylhexahydrohydrogen phthalate (manufactured by Osaka Organic Chemical Industry Ltd.), and 25 parts of 1-hydroxycyclohexyl phenyl ketone (manufactured by Ciba Geigy) was stirred in a UV-shielded vessel under a dry air stream at room temperature for 30 minutes to obtain Composition 1 shown in Table 2 as a homogeneous solution.

The compositions 2–8 shown in Table 2 were prepared in the same manner.

Example 9

A mixture of 154 parts of a dispersion of 1 g of silane-treated silica prepared in Example 7 and 2 parts of cumylperoxide (manufactured by Wako Pure Chemical Co.) was stirred under a dry air stream at room temperature for 30 minutes to obtain a homogeneous solution 1g. Composition 9 shown in Table 2 was prepared using this homogeneous solution in the same manner as in Example 8.

TABLE 2

| Composition | 1 | 2 | 3 | 4 | 5 | 6 | 7 | 8 | 9 |
|---|---|---|---|---|---|---|---|---|---|
| | | | | | | | | (parts by weight) | |
| Disperson of silane-treated silica | 1a | 1b | 1c | 1d | 1e | 1f | 1a | 1e | 1g |
| Amount | 520 | 500 | 400 | 400 | 200 | 200 | 1000 | 1000 | 154 |
| Unsaturated organic compound | | | | | | | | | |
| Dipentaerythritol hexacrylate | 400 | 300 | 400 | 400 | — | — | — | — | — |
| Ditrimethylolpropane tetracrylate | — | 200 | — | — | 100 | 100 | — | — | — |
| Hexanediol diacrylate | — | — | — | — | — | — | — | — | — |
| Urethane acrylate oligomer (UX2201) | — | — | — | — | 250 | 250 | — | — | — |
| Acryloylmorpholine | — | — | — | — | 150 | 150 | — | — | — |
| 2-Acryloxypropylhexahydrogen phthalate | 100 | — | 100 | 100 | — | — | — | — | — |
| Polymerization initiator | | | | | | | | | |
| 1-Hydroxycycloheyxyl phenyl ketone | 25 | 25 | 25 | 25 | 30 | 30 | 11 | 11 | — |
| Cumylperoxide | — | — | — | — | — | — | — | — | 2 |
| Ethyl acetate | — | — | — | — | 260 | 260 | — | — | — |
| Total | 1045 | 1025 | 1025 | 1030 | 1000 | 1000 | 1011 | 1011 | 156 |
| Solid components (%) | 69 | 76 | 79 | 79 | 86 | 60 | 36 | 36 | 65 |
| Silica in solid cornponents (%) | 19 | 7 | 19 | 19 | 6 | 9 | 70 | 77 | 20 |

Preparation of comparative composition

In order to clearly show the effects of the present invention Comparative Compositions shown in Table 3 were prepared in the following Examples.

A mixture of 450 parts of MEK—ST, 400 parts of dipentaerythritol hexaacrylate (manufactured by Nippon Kayaku Co.), 100 parts of 2-acryloxypropylhexahydrohydrogen phthalate (manufactured by Osaka Organic Chemical Industry Ltd.), and 25 parts of 1-hydroxycyclohexyl phenyl ketone (manufactured by Ciba Geigy) was stirred in a UV-shielded vessel under a dry air stream at room temperature for 30 minutes to obtain Comparative Composition 1 shown in Table 3 as a homogeneous solution.

Comparative Compositions 2–6 shown in Table 3 were prepared in the same manner.

TABLE 3

| Comparative Composition | 1 | 2 | 3 | 4 | 5 | 6 |
|---|---|---|---|---|---|---|
| | | | | | (parts by weight) | |
| Silica particles | | | | | | |
| MEK-ST | 450 | — | — | — | — | — |
| AEROSIL TT600 | — | 140 | — | — | — | — |
| Nipseal E220A | — | — | 140 | — | — | — |
| Sildex H122 | — | — | — | 140 | — | — |
| Polyunsaturated organic compound | | | | | | |
| Dipentaerythritol hexacrylate | 400 | 300 | 400 | 400 | 400 | — |
| Ditrimethylolpropane tetracrylate | — | 200 | — | — | — | 100 |
| Hexanediol diacrylate | | | | | | |
| Urethane acrylate oligomer (UX2201) | — | — | — | — | — | 250 |
| Monounsaturated organic compound | | | | | | |
| Acryloyl morpholine | — | — | — | — | — | 150 |
| 2-Acryloxypropyl-hexahydrogen phthalate | 100 | — | 100 | 100 | 100 | — |
| Photoinitiator | | | | | | |
| 1-Hydroxycyclohexyl phenyl ketone | 25 | 25 | 25 | 25 | 25 | 25 |

TABLE 3-continued

| Comparative Composition | 1 | 2 | 3 | 4 | 5 | 6 |
|---|---|---|---|---|---|---|
| | | | | | (parts by weight) | |
| Ethyl acetate | — | 360 | 360 | 360 | 180 | 180 |
| Total | 975 | 1025 | 1025 | 1030 | 700 | 700 |

Evaluation of Compositions

To demonstrate the effects of the present invention, the compositions prepared in the above examples were coated on the molded articles and their performances were evaluated.

1. Conditions for coating and curing

The compositions were coated on substrates using a bar coater No. 6 (manufactured by Yasuda Seiki Co.) to make a dry film with a thickness of 5 μm. After drying in a hot air dryer at 60° C. for 10 seconds, the films were irradiated with light at 1 J/cm$^2$ from a conveyer-type mercury lamp and stored for 24 hours at 25° C. before subjecting to evaluation, except that the composition of Example 9 in Table 4 was treated with heat in the hot air dryer at 80° C. for 30 minutes and allowed to cool to room temperature before evaluation.

2. Substrates

Glass plates were used for the evaluation of pencil hardness and transparency, and polycarbonate plates were used for the evaluation of abrasion resistance, adhesion, and accelerated weather resistance.

3. Evaluation methods

External appearance

Evaluated by naked eye observation

Light transmittance

The transmittance at a wavelength of 500 nm was measured using a spectrophotometer. The transmittance of films was determined after correction of the transmittance of the substrate.

Pencil hardness

The composition was cured on a glass substrate and the pencil hardness on the film was measured according to JIS K5400.

Taber abrasion test

The weight of abraded coating was measured, after an abrasion test according to ASTM D1175 55T using an abrasion wheel CS17 at a load of 1 kgf and a rotation of 500.

Adhesion

The adhesion test was carried out by a cellophane tape peeling test using a Go-board (1 mm square) according to JIS K5400. For the adhesion after hot moisture treatment the coated substrate was allowed to stand in a thermostat at 60° C. and RH 95% for 100 hours, before testing the adhesion by the same method.

Accelerated weather resistance

The test substrates were irradiated using an accelerated weather resistance tester, Q-UV (a trademark, manufactured by The Q-Panel Co.) at 30° C. for 500 hours to observe the outward appearance by naked eyes.

The results of tests are shown in Tables 4 and 5.

precipitate silica. After removing the organic components by decantation, the precipitate was dispersed in 100 parts of methyl ethyl ketone, followed by decantaion in the same manner as above. Silica powder was separated by repeating this procedure. The silica powder obtained was dried by treating with heat at 40° C. and 0.1 mmhg for 12 hours. A portion of the dried silica powder was mixed with KBr powder to measure IR spectrum. The IR spectrum chart obtained is shown in FIG. 1.

FIG. 1 shows, in addition to peaks at 805 $cm^{-1}$, 1000–1300 $cm^{-1}$, 1637 $cm^{-1}$, and 3,000–3,700 $cm^{-1}$ for silica, $v_{c=o}$ adsorption at 1,724 $cm^{-1}$ for acryloxy group and $v_{c=o}$ adsorption at 1,654 $cm^{-1}$ for urethane and thiourethane

TABLE 4

| Examples | 1 | 2 | 3 | 4 | 5 | 6 | 7 | 8 | 9 |
|---|---|---|---|---|---|---|---|---|---|
| External appearance of coated film* | T | T | T | F | T | T | T | T | T |
| Transmittance (%) | 94 | 90 | 91 | 35 | 95 | 95 | 95 | 95 | 95 |
| Pencil hardness | 8H | 7H | 6H | 7H | 4H | 3H | 5H | 3H | 6H |
| Taber test** | 21 | 30 | 44 | 400 | 300 | 400 | 50 | 100 | 30 |
| Adhesion | | | | | | | | | |
| Initial*** | 100 | 100 | 100 | 100 | 100 | 100 | 100 | 100 | 100 |
| After acceleration test | 100 | 100 | 100 | 100 | 100 | 100 | 100 | 100 | 100 |
| Accelerated weather resistance (Outward appearance) | None | None | None | None | None | None | None | None | None |

*T: transparent, F: frosty
**The abraded amount: mgx (1/10)
***The remaining squares (%) after peeling of the cellophane tape.

TABLE 5

| Comparative Examples | 1 | 2 | 3 | 4 | 5 | 6 |
|---|---|---|---|---|---|---|
| External appearance of coated film* | T | F | F | F | T | T |
| Transmittance (%) | 95 | 50 | 15 | 30 | 95 | 95 |
| Pencil hardness | 9H | 6H | 3H | 6H | 3H | 2H |
| Taber test** | 100 | 200 | 150 | 500 | 600 | 800 |
| Adhesion | | | | | | |
| Initial*** | 100 | 100 | 100 | 100 | 100 | 100 |
| After acceleration test | 100 | 100 | 100 | 100 | 100 | 100 |
| Accelerated weather resistance (Outward appearance) | Crack | Crack | Crack | Crack | None | None |

*T: transparent, F: frosty
**The abraded amount: mgx (1/10)
***The remaining squares (%) after peeling of the cellophane tape.

groups, indicating that the hydrolyzable silane with polymerizable unsaturated groups prepared in Reference Example 1 has fixed to silica particles.

The weight reduction from the constant weight at 110° C. in the air to the weight at 800° C., that is, the weight of combustible organic components in this dry silica powder, was determined by the theromogravimetric analysis (TGA), to find the reduction was 20%. The weight reduction of the silica powder separated from untreated MEK—ST under the same conditions was 3%. Based on the difference between the two measurements it can be concluded that at least 17% of the hydrolyzable silane with polymerizable unsaturated groups has fixed to silica particles. The amount of silane compounds fixed to the reactive silica particles prepared in Examples 2–6 was measured in the same manner. The results are shown in Table 6.

Evaluation of reactive silica particles

The quantities of silane compounds fixed to the reactive silica particles were measured by the following method.

Analytical Example 1

100 parts of the reactive silica particle dispersion prepared in Example 1 was centrifuged at 30,000 rpm for 5 hours to

TABLE 6

| Dispersion of silane-treated silica | Weight reduction of treated silica (%) | Weight reduction of untreated silica (%) | Amount of silane compound fixed to treated silica (%) |
|---|---|---|---|
| Example 1 | 20 | 3 | 17 |
| Example 2 | 15 | 2 | 13 |
| Example 3 | 14 | 2 | 12 |
| Example 4 | 14 | 6 | 8 |
| Example 5 | 18 | 3 | 15 |
| Example 6 | 25 | 3 | 22 |

The above results show that the silane compounds used in the present invention has fixed to the surface of silica particles.

As illustrated above, the composition of the present invention can produce coatings on various substrates exhibiting excellent characteristics, such as scratch resistance, weather resistance, adhesiveness, and curability, while satisfying a wide spectrum of performances from transparency to semi-transparency and providing a glossy surface as well as a frosty surface. The composition is useful as a material for scratch and weather resistent protective coatings on the surfaces of organic resin molded articles. It is also useful as a coating material for plastic substrates with poor heat resistance.

What is claimed is:

1. A curable composition comprising reactive silica particles comprising:
   (a) silica particles; and
   (b) an organic compound chemically bonded to the silica particles via a silyloxy group;
   wherein the organic compound has
      (i) a polymerizable unsaturated group
      (ii) a group represented by the following formula (1);

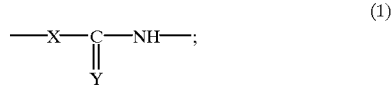
(1)

and
      (iii) a group represented by the following formula (2);

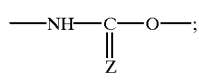
(2)

wherein
X represents a group selected from —NH—, —O—, and —S—;
Y represents a group selected from oxygen and sulfur;
Y represents sulfur if X represents oxygen; and
Z represents a group selected from oxygen and sulfur.

2. The composition of claim 1, further comprising at least one polymerizable compound.

3. The composition of claim 1, wherein X represents —S—, and Y and Z both represent oxygen.

4. The composition of claim 1, wherein said polymerizable unsaturated group is an acrylate, methacrylate, or vinyl ether group.

5. The composition of claim 1, wherein the particles of component (a) have an average diameter of about 0.00–20 μm.

6. A coating obtained by curing a composition comprising:
   (x) reactive silica particles;
   (y) about 0–2,000 parts by weight, per 100 parts by weight of component (x), of a poly unsaturated organic compound; and
   (z) about 0–1,000 parts by weight, per 100 parts by weight of component (x), of a mono unsaturated organic compound;
   wherein said reactive silica particles comprise
      (a) silica particles; and
      (b) an organic compound chemically bonded to the silica particles via a silyloxy group;
   wherein the organic compound has
      (i) a polymerizable unsaturated group
      (ii) a group represented by the following formula (1);

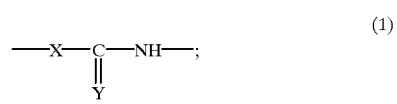
(1)

and
      (iii) a group represented by the following formula (2);

(2)

wherein
X represents a group selected from —NH—, —O—, and —S—;
Y represents a group selected from oxygen and sulfur;
Y represents sulfur if X represents oxygen; and
Z represents a group selected from oxygen and sulfur.

7. The coating of claim 6, wherein said composition further comprises 0.1–10 parts of a polymerization initiator per 100 parts of curable composition.

8. The coating of claim 6, wherein X represents —S—, and Y and Z both represent oxygen.

9. The coating of claim 6, wherein said polymerizable unsaturated group is an acrylate, methacrylate, or vinyl ether group.

10. The coating of claim 6, wherein the particles of component (a) have an average diameter of about 0.001–20 μm.

11. The coating of claim 6, wherein the coating has a thickness of about 0.1–400 μm.

12. The coating of claim 6, wherein the coating is a coating for plastic, metal, wood, paper, glass, or slate.

* * * * *

UNITED STATES PATENT AND TRADEMARK OFFICE
CERTIFICATE OF CORRECTION

PATENT NO. : 6,160,067                                                                           Page 1 of 1
DATED : December 12, 2000
INVENTOR(S) : Eriyama et al.

It is certified that error appears in the above-identified patent and that said Letters Patent is hereby corrected as shown below:

<u>Column 25, claim 5,</u>
Should read -- 5. The composition of claim 1, wherein the particles of component (a) have an average diameter of about 0.001—20 μm. --

Signed and Sealed this

Twenty-fifth Day of December, 2001

Attest:

Attesting Officer

JAMES E. ROGAN
Director of the United States Patent and Trademark Office